(12) United States Patent
Makriyannis et al.

(10) Patent No.: US 7,173,027 B2
(45) Date of Patent: Feb. 6, 2007

(54) RECEPTOR SELECTIVE CANNABIMIMETIC AMINOALKYLINDOLES

(75) Inventors: Alexandros Makriyannis, Mystic, CT (US); Hongfeng Deng, Acton, MA (US)

(73) Assignee: University of Connecticut, Farmington, CT (US)

(*) Notice: Subject to any disclaimer, the term of this patent is extended or adjusted under 35 U.S.C. 154(b) by 265 days.

(21) Appl. No.: 10/470,359

(22) PCT Filed: Jan. 29, 2002

(86) PCT No.: PCT/US02/02501

§ 371 (c)(1),
(2), (4) Date: Jul. 25, 2003

(87) PCT Pub. No.: WO02/060447

PCT Pub. Date: Aug. 8, 2002

(65) Prior Publication Data

US 2004/0077851 A1    Apr. 22, 2004

Related U.S. Application Data

(60) Provisional application No. 60/264,855, filed on Jan. 29, 2001.

(51) Int. Cl.
| | |
|---|---|
| C07D 401/06 | (2006.01) |
| C07D 401/14 | (2006.01) |
| C07D 413/06 | (2006.01) |
| A61K 31/4439 | (2006.01) |
| A61K 31/4709 | (2006.01) |
| A61K 31/472 | (2006.01) |
| A61K 31/496 | (2006.01) |
| A61K 31/498 | (2006.01) |
| A61K 31/5377 | (2006.01) |

(52) U.S. Cl. .................. 514/235.2; 514/255; 514/311; 514/323; 544/143; 544/144; 544/355; 546/176; 546/201

(58) Field of Classification Search ................ 544/143, 544/144; 546/201; 514/235.2, 323
See application file for complete search history.

(56) References Cited

U.S. PATENT DOCUMENTS

| | | | |
|---|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,838,131 A | 9/1971 | Gauthier |
| 3,656,906 A | 4/1972 | Bullock |
| 3,886,184 A | 5/1975 | Matsumoto et al. |
| 3,897,306 A | 7/1975 | Vldic |
| 3,915,996 A | 10/1975 | Archer |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan |
| 4,176,233 A | 11/1979 | Archer et al. |
| 4,179,517 A | 12/1979 | Mechoulam et al. |
| 4,188,495 A | 2/1980 | Althuis et al. |
| 4,208,351 A | 6/1980 | Archer et al. |
| 4,278,603 A | 7/1981 | Thakkar |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya et al. |
| 4,876,276 A | 10/1989 | Mechoulam et al. |
| 4,885,295 A | 12/1989 | Bell |
| 5,053,548 A | 10/1991 | Tanaka et al. |
| 5,068,234 A | 11/1991 | D'Ambra et. al. |

(Continued)

FOREIGN PATENT DOCUMENTS

EP    0276732    8/1988

(Continued)

OTHER PUBLICATIONS

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; Coden: JMCMAR; ISSN: 0022-2623; XP002040932.

(Continued)

Primary Examiner—Fiona T. Powers
(74) Attorney, Agent, or Firm—Alix, Yale & Ristas, LLP

(57) ABSTRACT

Disclosed are cannabimimetic aminoalkylindole compounds and methos for their manufacture. The disclosed compounds are surprisingly potent and selective cannabinoinds. Also disclosed are methods of using the disclosed compounds, including use of the disclosed compounds to stimulate a cannabinoid receptor, to provide a physiological effect in an animal or individual and to treat a condition in an animal or individual.

11 Claims, No Drawings

U.S. PATENT DOCUMENTS

| | | |
|---|---|---|
| 5,147,876 A | 9/1992 | Mizuchi et al. |
| 5,223,510 A | 6/1993 | Gubin et al. |
| 5,284,867 A | 2/1994 | Kloog et al. |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam et al. |
| 5,532,237 A | 7/1996 | Gallant et al. |
| 5,538,993 A | 7/1996 | Mechoulam et al. |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |
| 5,624,941 A | 4/1997 | Barth et al. |
| 5,635,530 A | 6/1997 | Mechoulam et al. |
| 5,688,825 A | 11/1997 | Makriyannis et al. |
| 5,744,459 A | 4/1998 | Makriyannis et al. |
| 5,747,524 A | 5/1998 | Cullinan et al. |
| 5,804,601 A | 9/1998 | Kato et al. |
| 5,817,651 A | 10/1998 | D'Ambra et al. |
| 5,872,148 A | 2/1999 | Makriyannis et al. |
| 5,874,459 A | 2/1999 | Makriyannis et al. |
| 5,925,628 A | 7/1999 | Lee et al. |
| 5,925,768 A | 7/1999 | Barth et al. |
| 5,932,610 A | 8/1999 | Shohami et al. |
| 5,948,777 A | 9/1999 | Bender et al. |
| 6,013,648 A | 1/2000 | Rinaldi et al. |
| 6,028,084 A | 2/2000 | Barth et al. |
| 6,096,740 A | 8/2000 | Mechoulam et al. |
| 6,127,399 A | 10/2000 | Yuan |
| 6,166,066 A | 12/2000 | Makriyannis et al. |
| 6,284,788 B1 | 9/2001 | Mittendorf et al. |
| 6,391,909 B1 | 5/2002 | Makriyannis et al. |
| 6,579,900 B2 | 6/2003 | Makriyannis et al. |
| 6,610,737 B1 | 8/2003 | Garzon et al. |
| 2002/0119972 A1 | 8/2002 | Leftheris et al. |
| 2002/0173528 A1 | 11/2002 | Fride et al. |
| 2003/0120094 A1 | 6/2003 | Makriyannis et al. |
| 2003/0149082 A1 | 8/2003 | Makriyannis et al. |
| 2004/0077649 A1 | 4/2004 | Makriyannis et al. |
| 2004/0077851 A1 | 4/2004 | Makriyannis et al. |
| 2004/0087590 A1 | 5/2004 | Makriyannis et al. |

FOREIGN PATENT DOCUMENTS

| | | |
|---|---|---|
| EP | 0444451 | 9/1991 |
| EP | 0471609 | 6/1993 |
| EP | 0737671 | 10/1996 |
| EP | 0860168 | 9/2001 |
| FR | 2240003 | 5/1975 |
| FR | 2735774 | 1/2001 |
| GB | 2027021 A | 2/1980 |
| JP | 57098228 | 6/1982 |
| JP | 2304080 | 12/1990 |
| WO | WO 93/13099 | 7/1993 |
| WO | WO 97/00860 | 1/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/058636 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

Beltramo M., Stella N., Calignano A., Lin S. Y., Makriyannis A., Piomelli D; "Functional Role Of High-Affinity Anandamide Transport, as Revealed By Selective Inhibition"; Science; vol. 277; 1094-1097; 1997.

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998). (abstract only).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Bracey, M et al, Structural Adaptations in a Membrane Enzyme That Terminates Endocannabinoid Signaling. Science 2002; 298(5599): 1793-1796.

Brenneisen R, Pgli A, Elsohly MA, Henn V. Spiess Y: The effect of orally and rectally administered 9-tetrahydrocannabinol on spasticity, a polit study with 2 patients. Int. J. Clin Pharmacol Ther. (1996) 34:446-452. (abstract only).

Brown et al; "Synthesis and hydroboration of (−)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141-149.

Burstein et al; "detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

Calignano A, La Rana G. Diuffrida A, Piomelli D; "Control of pain initiation by endogenous cannabinoids"; Nature (1998) 394:277-291. (abstract only).

Calignano A., La Rana G., Beltramo, M., Makriyannis A., Piomelli D; "Potentiation of Anandamide Hypotension by the Transport Inhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option in the management of pain? A qualitative systematic review"; BMJ. Jul. 7, 2001;323(7303):13-6.

Charalambous A. et al; "5'-azido 8-THC: A Novel Photoaffinity Label for the Canannabinoid Receptor"; J. Med. Chem., 35, 3076-3079 (1992).

Charalambous A. et al; "Pharmacological evaluation of halogenated . . . "; Pharmacol. Biochem. Behav.; vol. 40; No. 3; 509-512; 1991.

Cheng et al; "Relationship Between the Inhibition Constant (Ki) and the concentration of inhibitor which causes 50% Inhibition (I50) of an Enzymatic Reaction"; Biochem. Pharmacol., 22, 3099-3102, (1973) (abstract only ).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel Electrophilic N-Amidation via electron deficient complexes: action of ferric chloride on N-acetyloxyamides"; Tetrahedron Letters; 30(6); 715-718; 1989.

Colombo G, Agabio R, Diaz G. et al; "Appetite suppression and weight loss after the cannabinoid antagonist SR141716"; Life Sci. (1998) 63-PL13-PL117. (abstract only).

Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Desarnaud F., Cadas H., Piomelli D.; "Ananadamide amidohydrolase activity in rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; Coden: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

Devane, W.A. et al; "Determination and Characterization of a Cannabinoid Receptor ina Rat Brain"; Mol. Pharmacol., 34, 605-613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

*1* Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-Δ9-Tetrahydrocannabinol and Four of its Isomers"; J. Amer. Chem. Soc. 1967, 89(23), 5934-5941.

Fahrenholtz; "The synthesis of 2 metabolites of (−)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

Fride, E. & Mechoulam, R.; "Pharmacological activity of the cannabinoid receptor agonist, anandamide, a brain constituent"; European Journal od Pharmacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

Hampson, A.J., Grimaldi M. Axpirod J. Wink D; "Cannabidiol and (−) 9 tetrahydrocannabinol are neuroprotective antioxidants"; Proc. Natl Acad Sci. USA (Jul. 1998) 95; 8268-8273.

Hargreaves, K. et al; "A new sensitive method for measuring thermal nociception in cutaneous hyperalgesia"; Pain; 32; 77-88; (1988) (abstract only).

Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of escherichia coli outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53939), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Kaminski NE; "Regualtion of the cAMP cascade, gene expression and immune function by cannabinoid receptors"; J Neuroimmunol. Mar. 15, 1998; 83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; Coden: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

*1* Lan, R et al; "Structure activity relationships of pyrazole derivatives as cannabinoid receptor antagonists"; J. Med. Chem.; vol. 42(4); 769-776; (1999).

Lavalle et al; "Efficient conversion of (1R, 5R)-(+)-alpha-pinene to (1S, 5R)-(−)-nonpinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyl-lithium and lithium diisopropylamide in the metalations of N,N-dialkyltouamides"; J. Org. Chem.; 38(9); 1668-1674 (1973).

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; "Synthesis of the individual, pharmacologically distinct enantiomers of a tetrahydrocannabinol derivative"; Tetrahedron Asymmetry; 1: 311-314; (1990) (abstract only).

Melvin et al; "Structure-activity relationships for cannabinoid receptor-binding and analgesic activity: studies of bicyclic cannabinoid analogs"; Mol. Pharmacol.; 44(5); 1008-1015 (1993).

Merck Index; 11th edition; "Tetrahydrocannabinols" compound No. 9142; 1989.

Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Papahatjis et al; "A new ring-formula methodology for the synthesis of conformationally constrained bioacitve molecules"; Chemistry Letters, 192; (2001).

Papahatjis et al; "Pharmacophoric requirements for cannabinoid side chains: multiple bonds and C1'-substituted delta8-tetrahydrocannabinols"; J. Med. Chem.; 41(7); 1195-1200; (1998).

*1* Pertwee et al; "AM630, a competitive cannabinoid receptor antagonist"; Life Sci. 1995, 56(23/24), 1949-1955; XP 000653566.

*1* Pertwee et al; "Pharmacological characterization of three novel cannabinoid receptor agonists in the mouse isolated vas deferens"; Eur. J. Pharmacol. 1995, 284, 241-247; XP-001041044.

Pertwee; Pharmacology of cannabinoid CB1 and CB2 receptors; Pharmacol. Ther., vol. 74(2); pp. 129-180; (1997); XP002226467.

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labellled Compounds; vol. 11(4); 551-575; 1975; XP002123229.

Reggio et al; Characterization of a region of steric interference at the cannabinoid receptor using the active analog approach, J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Richardson JD, Aanonsen I, Hargreaves KM; "Antihyperalgesic effects of spinal cannabinoids"; Eur. J. Pharmacol. (1998) 346:145-153.

Richardson JD, Kilo S. Hargreaves KM; "Cannabinoids reduce hyperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmons et al; "SR141716A, potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Snatus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

*1* Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

*1* Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

*1* Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Smith P.B. et al; "The pharmacological activity of anandamide, a putative endogenous cannabinoid, in mice"; Journal of Pharmacology and Experimental Therapeutics; vol. 270(1):219-227; 1994.

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibits N- and P/Q type calcium channels in cultured rat hippocampal neurons"; Journal of Neurophysiology; 78(1); 43-50; 1997 (abstract only).

Watanabe, T.; Miyaura, N.; and Suzuki, A.; "Synthesis of Sterically Hindered Biaryls via the Palladium Catalzed Cross-Coupling Reaction of Arylboronic Acids or their Esters with Haloarenes"; Synlett 1992, 207-210.

*1* Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic interest"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydroxyhexahydrocannabinols. Synthesis, some behavioral and analgesic properties, and comparison with the tetrahydrocannabinols"; J. Med. Chem.; 19(9); 1165-1167; (1976).

*1* Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(−)-11-hydroxy-7'-isothiocyanato-1'-1'dimethylheptyl-delta8-THC:a novel probe for the cannabinoid receptor in the brain"; J. Med. Chem.; 37(23); 3867-3870; (1994).

*1* Supplementary Partial European Search Report for European Patent Application No. EP 02 70 2097 dated Jun. 28, 2004, pp. 1-3.

*1* Pacheco M, et al; "Aminoalkylindoles: Actions On Specific G-Protein-Linked Receptors"; J. Pharmacol. Exp. Ther.; vol. 257, No. 1, pp. 170-183 and 172 Table (1991).

*1* Tetko, I. V. et al; "Volume Learning Algoritm Artificial Neural Networks For 3D QSAR Studies"; J. Med. Chem.; vol. 44, No. 15 (2001) pp. 2411-2420, 2413, 2414 Table 1.

RECEPTOR SELECTIVE CANNABIMIMETIC AMINOALKYLINDOLES

This application is the National Stage of International Application No. PCT/US502/02501, filed Jan. 29, 2002, which claims the benefit of U.S. Provisional Application No. 60/264,855, filed Jan. 29, 2001, the contents of each of which are incorporated herein by reference in their entirety.

FIELD OF THE INVENTION

The present invention relates generally to indole compounds exhibiting cannabimimetic activity. The present invention is more particularly concerned with new and improved aminoalkylindole compounds exhibiting high binding affinity for at least one cannabinoid receptor and/or high selectivity for one cannabinoid receptor, pharmaceutical preparations employing these compounds and methods of administering therapeutically effective amounts of these compounds to provide a physiological effect.

BACKGROUND OF THE INVENTION

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects.

There is considerable interest in developing cannabimimetic compounds possessing high affinity for one of the CB1 or CB2 receptors. Such compounds may offer a rational therapeutic approach to a variety of disease conditions. One class of cannabimimetic compound encompasses indole derivatives such as the well-known aminoalkylindoles represented by WIN 55212-2 {(R)-(+)-[2,3-dihydro-5-methyl-3-[(4-morpholinyl)methyl]-pyrrolo[1,2,3-de]-1,4-benzoxazin-6-yl](1-napthalenyl)methanone}. Aminoalkylindoles of this type typically have a carbon linked alkylheterocyclic substituent at the indole-1 position, which is believed to be important for their cannabimimetic activities. These known materials are not selective for preferential activation of one of the CB1 or CB2 receptors.

SUMMARY OF THE INVENTION

It has now been found that certain aminoalkylindoles possess surprising cannabimimetic properties, including selectivity for the CB1 or CB2 cannabinoid receptor. Broadly, in one aspect of the invention the novel cannabimimetic compounds can be represented by the structural formula I below, physiologically acceptable salts, diasteromers, enantiomers, double bond isomers or mixtures thereof.

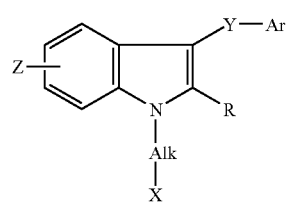

structural formula 1 wherein:

Z comprises at least one substituent independently chosen from hydrogen; halogen; hydroxy; alkoxy; thioalkoxy; aryl and lower alkyl;

Alk comprises an alkyl group or a substituted alkyl group;

X comprises a 5, 6 or 7 member heterocyclic ring, including at least one heteroatom independently selected from oxygen, nitrogen and sulfur; a substituted 5, 6 or 7 member heterocyclic ring, including at least one heteroatom independently selected from oxygen, nitrogen and sulfur; a bicyclic ring; or a bicyclic ring including at least one heteroatom independently selected from oxygen, nitrogen and sulfur;

R comprises hydrogen, CN, CHO, an alkyl group or a substituted alkyl group;

Y comprises carbonyl, CH=CH (cis or trans), CONH or C=NH; and

Ar comprises adamantyl; azoadamantyl; phenyl; napthyl; 9-anthracenyl; pyridinyl; quinolinyl; isoquinolinyl; quinazolinyl; an aliphatic bicyclic ring; an azabicyclic ring; a heterobicyclic ring; any of the above with no more than two substituents each independently selected from amino, halogen, hydroxy, nitro, nitroso, azido, isothiocyanato, cyano, COOH, CONR$^3$R$^4$ where R$^3$ and R$^4$ each independently comprise H, alkyl or substituted alkyl, NCOR$^3$R$^4$ where R$^3$ and R$^4$ each independently comprise H, alkyl, substituted alkyl, CF$_3$, SO$_2$NR$^3$R$^4$ where R$^3$ and R$^4$ each independently comprise H, alkyl, substituted alkyl or CF$_3$; or a salt of any of the above.

In one preferred aspect of the invention the novel compounds can be represented by structural formula I above, wherein:

wherein:

Z comprises hydrogen;

Alk comprises a C$_{1-2}$alkyl group;

X comprises a 5, 6 or 7 member heterocyclic ring, including at least one heteroatom independently selected from oxygen, nitrogen and sulfur; a substituted 5, 6 or 7 member heterocyclic ring, including at least one heteroatom independently selected from oxygen, nitrogen and sulfur; a bicyclic ring; or a bicyclic ring including at least one heteroatom independently selected from oxygen, nitrogen and sulfur;

R comprises hydrogen;

Y comprises carbonyl; and

Ar comprises adamantyl; azoadamantyl; phenyl; napthyl; 9-anthracenyl;

pyridinyl; quinolinyl; isoquinolinyl; quinazolinyl; an aliphatic bicyclic ring; an azabicyclic ring; any of the above with no more than two substituents each independently selected from amino, halogen, hydroxy, nitro, nitroso, azido, isothiocyanato, cyano, COOH, CONR³R⁴ where R³ and R⁴ each independently comprise H, alkyl or substituted alkyl, NCOR³R⁴ where R³ and R⁴ each independently comprise H, alkyl, substituted alkyl, CF₃, SO₂NR³R⁴ where R³ and R⁴ each independently comprise H, alkyl, substituted alkyl or CF₃; or a salt of any of the above.

In another preferred aspect of the invention the novel compounds can be represented by structural formula II below,

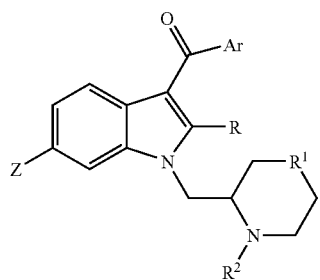

structural fromula II wherein:
Z comprises hydrogen;
R comprises hydrogen;
R¹ comprises N, O, S or CH₂;
R² comprises H, alkyl, CF₃, CH₂C≡CH, CH₂CH═CH₂ or CH₂Ph; and
Ar comprises adamantyl; azoadamantyl; phenyl; napthyl; 9-anthracenyl;
pyridinyl; quinolinyl; isoquinolinyl; quinazolinyl; an aliphatic bicyclic ring; an azabicyclic ring; any of the above with no more than two substituents each independently selected from amino, halogen, hydroxy, nitro, nitroso, azido, isothiocyanato, cyano, COOH, CONR³R⁴ where R³ and R⁴ each independently comprise H, alkyl or substituted alkyl, NCOR³R⁴ where R³ and R⁴ each independently comprise H, alkyl, substituted alkyl, CF₃, SO₂NR³R⁴ where R³ and R⁴ each independently comprise H, alkyl, substituted alkyl or CF₃; or a salt of any of the above.

Unless otherwise specifically defined, "alkyl" refers to a linear, branched or cyclic alkyl group having from 1 to about 9 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated and substituted or unsubstituted. Unless otherwise specifically defined, "lower-alcohol" refers to the general formula alkyl-OH. Unless otherwise specifically defined, "alkoxy" refers to the general formula —O-alkyl. Unless otherwise specifically defined, "alkylmercapto" refers to the general formula —S-alkl. Unless otherwise specifically defined, "alkylamino" refers to the general formula —(NH)-alkyl. Unless otherwise specifically defined, "di-alkylamino" refers to the general formula —N-(alkyl)₂. Unless otherwise specifically defined, an aromatic ring is an unsaturated ring structure, substituted or unsubstituted, that includes only carbon as ring atoms. Unless otherwise specifically defined, a heteroaromatic ring is an unsaturated ring structure, substituted or unsubstituted, that has carbon atoms and one or more heteroatoms, including oxygen, nitrogen and/or sulfur, as ring atoms, for example, pyridine, furan, quinoline, and their derivatives. Unless otherwise specifically defined, a carbocyclic ring is a saturated ring structure, substituted or unsubstituted, that includes only carbon as ring atoms, for example, cyclohexane. Unless otherwise specifically defined, a heterocyclic ring is a saturated ring structure, substituted or unsubstituted, that has carbon atoms and one or more heteroatoms, including oxygen, nitrogen and/or sulfur, as ring atoms, for example, piperidine, morpholine, piperazine, and their derivatives. Unless otherwise specifically defined, an aliphatic bicyclic ring is a polycyclic structure, substituted or unsubstituted, having about 6 to about 12 ring atoms that includes only carbon as ring atoms, for example bicyclohexane and bicyclodecane. Unless otherwise specifically defined, a heterobicyclic ring is a polycyclic structure, substituted or unsubstituted, having about 6 to about 12 ring atoms that has carbon atoms and one or more heteroatoms, including oxygen, nitrogen and/or sulfur, as ring atoms, for example tropane.

Substituent groups useful in the invention are those groups that do not significantly diminish the biological activity of the inventive compound. Unless otherwise specifically defined, substituent groups that do not significantly diminish the biological activity of the inventive compound include, for example, alkyl, substituted alkyl, phenyl, substituted phenyl, OH, NH₂, alkoxy, halogen, CF₃, CN, NCS, azido, CONR³R⁴ where R³ and R⁴ each independently comprise H, alkyl or substituted alkyl, NCOR³R⁴ where R³ and R⁴ each independently comprise H, alkyl, substituted alkyl, CF₃, SO₂NR³R⁴ where R³ and R⁴ each independently comprise H, alkyl, substituted alkyl or CF₃, sulfonamide, or lower alcohol.

Some of the inventive cannabinoid compounds exhibit high affinity for the CB1 and/or CB2 cannabinoid receptor. More specifically, some of the inventive analogs showed similar or higher receptor binding affinity than the well-known indole cannabinoid WIN 5521 2-2. Thus, another aspect of the invention is use of at least one of the inventive compounds to interact with a cannabinoid receptor.

Further, some of the inventive cannabinoid compounds show a surprisingly higher selectivity for one of the CB1 or CB2 cannabinoid receptors. These inventive selective compounds are able to interact with one cannabinoid receptor, for example the CB2 receptor, without affecting the CB1 cannabinoid receptor to the same degree. More specifically, some of these compounds show not only comparable cannabimimetic activity with the compound WIN 55212-2, but also a surprisingly higher selectivity for one of the CB1or CB2 receptors. Therefore, still another aspect of the invention is use of at least one of the inventive compounds to preferentially interact with one cannabinoid receptor.

Some of the inventive cannabinoid compounds can act as high affinity modulators for the CB2 cannabinoid receptor. The inventive cannabinoid compounds therefore are potential therapeutic agents through the modulation of a cannabinoid receptor.

Some of the novel cannabinoid compounds described herein may be agonists for at least one of the cannabinoid receptors. The inventive cannabinoid agonists interact with the at least one cannabinoid receptor binding site to initiate a physiological or a pharmacological response characteristic of that receptor. Therefore, a further aspect of the invention is use of at least one of the inventive compounds to initiate an agonistic response from a cannabinoid receptor.

Some of the novel compounds described herein may be cannabinoid receptor antagonists. The inventive cannabinoid antagonists interact with the CB1 and/or CB2 cannabinoid receptor binding site to block other ligands from the receptor binding site without initiating a physiological or a pharmacological response characteristic of that receptor.

Thus, cannabinoid antagonists typically oppose the cannabinoid receptor site response characteristics initiated by cannabinoid agonists. Therefore, a further aspect of the invention is use of at least one of the inventive compounds to oppose initiation of an agonistic response from a cannabinoid receptor.

The inventive cannabinoid compounds described herein, and physiologically acceptable salts thereof, have pharmacological properties when administered in therapeutically effective amounts for providing a physiological response in individuals and/or animals. Thus, another aspect of the invention is the administration of a therapeutically effective amount of at least one of the inventive cannabimimetic compounds, or a physiologically acceptable salt thereof, to an individual or animal to provide a physiological response.

Additionally, some of the halogen containing analogs, for example those analogs comprising iodide and fluoride, are potential radioactive probes for imaging in vivo the distribution of cannabinoid receptors.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DESCRIPTION OF A PREFERRED EMBODIMENT

As used herein, a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Such discernible increase or decrease in stimulation of cannabinoid receptors can provide a physiological effect in the individual or animal.

Physiological effects that result from CB1 cannabinoid receptor interaction with agonist compounds include relief of pain, peripheral pain, neuropathic pain, glaucoma, epilepsy and nausea such as associated with cancer chemotherapy; appetite enhancement; selective killing of glioma and breast cancer cells; alleviation of the symptoms of neurodegenerative diseases including Multiple Sclerosis, Parkinson's Disease, Huntington's Chorea and Alzheimer's Disease, reduction of fertility; prevention or reduction of diseases associated with motor function such as Tourette's syndrome; neuroprotection; suppression of memory and peripheral vasodilation. Physiological effects that result from CB1 cannabinoid receptor interaction with antagonist compounds include appetite suppression; memory enhancement; beneficial effects in mental disorders such as schizophrenia and depression; and beneficial effects in endotoxic and hypotensive shock. Physiological effects that result from CB2 cannabinoid receptor interaction with agonist compounds include relief of pain, peripheral pain, neuropathic pain, glaucoma, epilepsy and nausea such as associated with cancer chemotherapy; selective killing of glioma and breast cancer cells; alleviation of the symptoms of neurodegenerative diseases including Multiple Sclerosis, Parkinson's Disease, Huntington's Chorea and Alzheimer's Disease, reduction of fertility; prevention or reduction of diseases associated with motor function such as Tourette's syndrome; prevention or reduction of inflammation; neuroprotection; and suppression of the immune system. Physiological effects that result from CB2 cannabinoid receptor interaction with antagonist compounds include enhancement of the immune system and peripheral vasoconstriction. Typically a "therapeutically effective amount" of the novel compounds ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of compound will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

The prepared cannabimimetic indole derivatives can generally be described with reference to exemplary structural formulas 1 and 2 below.

The inventive compounds of exemplary structural formula 1 include both racemics and two enantiomers and are listed in TABLE 1.

exemplary structural formula 1

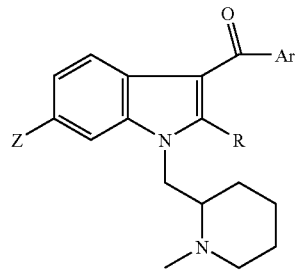

It should be noted that alk-X for all of the materials of TABLE 1 was 1-(N-methyl-2-piperidinyl)methyl.

TABLE 1

| | | | | $K_i$ nM | |
|---|---|---|---|---|---|
| analog | Z | R | Ar | CB1 | CB2 |
| 2-7(R, S) | H | H | 2-iodo-5-nitrophenyl | 403 | 5.7 |
| 2-7(R) | H | H | 2-iodo-5-nitrophenyl | 285 | 0.53 |

TABLE 1-continued

| | | | | Ki nM | |
|---|---|---|---|---|---|
| analog | Z | R | Ar | CB1 | CB2 |
| 2-7(S) | H | H | 2-iodo-5-nitrophenyl | 906 | 9.5 |
| 2-7(R, S) human | H | H | 2-iodo-5-nitrophenyl | | 1.6 |
| 2-24(R) | H | H | 2-iodophenyl | 1.8 | 2.1 |
| 2-24(S) | H | H | 2-iodophenyl | 561 | 583 |

Surprisingly, and as exemplified by compounds 2-7 and 2-24, in all cases the + configuration (R configuration) has a higher selectivity for the CB2 receptor and a higher affinity for the CB2 receptor.

Compound 2-7 was tested for binding affinity to human CB2 receptors using the below described procedure with human tissue samples. That compound was found to be a surprisingly potent cannabinoid.

exemplary structural formula 2

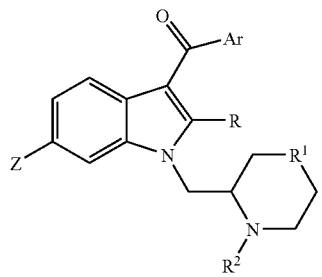

TABLE 2

| | | | | | | Ki nM | |
|---|---|---|---|---|---|---|---|
| analog | Z | R | $R^1$ | $R^2$ | Ar | CB1 | CB2 |
| 2-25 | H | H | O | $CH_2Ph$ | 2-iodo-methylphenyl | 1217 | 1800 |
| 2-26 | H | H | O | $CH_2Ph$ | 4-iodo-3-methyl-nitrophenyl | 4212 | 1431 |
| 2-27 | H | H | O | $CH_2Ph$ | 2-iodo-3-methyl-nitrophenyl | 2383 | 927.5 |
| 2-28 | H | H | O | $CH_3$ | 2-iodo-methylphenyl | 27.93 | 226.3 |
| 2-29 | H | H | O | $CH_3$ | 4-iodo-3-methyl-nitrophenyl | 848.1 | 48.45 |
| 2-30 | H | H | O | $CH_3$ | 2-iodo-3-methyl-nitrophenyl | 464.3 | 153.5 |
| 2-31 | H | H | O | $CH_3$ | methylnaphthyl | 5.696 | 26.56 |

TABLE 2-continued
| analog | Z | R | R¹ | R² | Ar | Ki nM CB1 | Ki nM CB2 |
|---|---|---|---|---|---|---|---|
| 2-32 (R,S) | H | H | CH₂ | CH₃ | 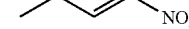 | 239.4 (R,S) | 3.411 (R,S) |
| 2-32 (R) | H | H | CH₂ | CH₃ | 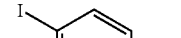 | 139.7 (R) | 1.416 (R) |
| 2-32 (S) | H | H | CH₂ | CH₃ |  | 2029 (S) | 160.5 (S) |
| 2-32 (R,S) human | H | H | CH₂ | CH₃ | 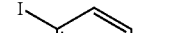 | | 13.60 (R,S), Human |
| 2-32 (R) human | H | H | CH₂ | CH₃ | 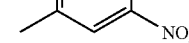 | | 6.688 (R), Human |
| 2-33 | H | H | CH₂ | CH₃ | 1-Adamantyl | 11.93 | 4.804 |
| 2-33 human | H | H | CH₂ | CH₃ | 1-Adamantyl | | 2.321 Human |
| 2-34 (R,S) | H | H | CH₂ | CH₃ | 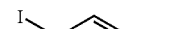 | 2.889 (R,S) | 3.345 (R,S) |
| 2-34 (R) | H | H | CH₂ | CH₃ |  | 1.573 (R) | 1.558 (R) |
| 2-34 (S) | H | H | CH₂ | CH₃ |  | 14.17 (S) | 6.789 (S) |
| 2-34 (R,S) human | H | H | CH₂ | CH₃ |  | | 2.488 Human |
| 2-35 | H | H | CH₂ | CH₃ |  | 14.36 | 20.93 |
| 2-36 | H | H | CH₂ | CH₃ |  | 133.1 | 8.532 |
| 2-37 | H | H | CH₂ | CH₃ |  | 3541 | 836.6 |

TABLE 2-continued
| analog | Z | R | R¹ | R² | Ar | Ki nM CB1 | CB2 |
|---|---|---|---|---|---|---|---|
| 2-38 | H | H | CH₂ | CH₃ | 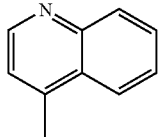 | 719.3 | 747.5 |
| 2-39 | H | H | CH₂ | CH₃ | 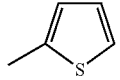 | 41.44 | 19.53 |
| 2-40 | H | H | CH₂ | CH₃ | 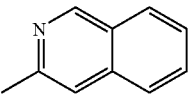 | 28.65 | 14.54 |
| 2-41 | H | H | CH₂ | CH₃ | 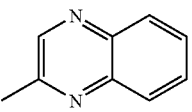 | 157.8 | 159.7 |
| 2-42 | H | H | CH₂ | CH₃ | 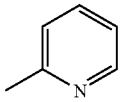 | 421.4 | 147.2 |
| 2-43 | H | H | CH₂ | CH₃ | 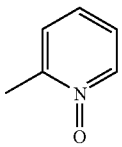 | 8816 | 1858 |
| 2-44 | H | H | CH₂ | CH₃ | 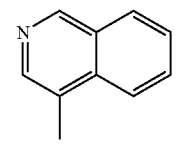 | 16.94 | 7.037 |
| 2-45 | H | H | CH₂ | CH₃ | 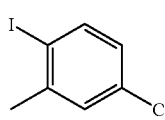 | 418.5 | 15.82 |
| 2-46 | H | H | CH₂ | CH₃ | 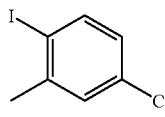 Hydrochloride | 338.7 | 15.41 |
| 2-47 | H | H | CH₂ | CH₃ | 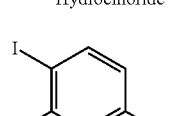 Hydrochloride | 240.2 | 18.76 |
| 2-48 | H | H | CH₂ | CH₃ | 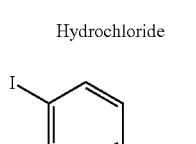 | 390.0 | 47.17 |

TABLE 2-continued

| analog | Z | R | R$^1$ | R$^2$ | Ar | Ki nM CB1 | CB2 |
|---|---|---|---|---|---|---|---|
| 2-49 | H | H | CH$_2$ | CH$_3$ | 4-iodo-3-methylphenol | 29.07 | 18.63 |
| 2-50 | H | H | CH$_2$ | CH$_3$ | 4-iodo-3-methylaniline | | |
| 2-51 | H | H | CH$_2$ | CH$_3$ | N-(4-iodo-3-methylphenyl)acetamide | | |
| 2-52 | H | H | CH$_2$ | CH$_3$ | N-(4-iodo-3-methylphenyl)trifluoroacetamide | | |
| 2-53 | H | H | CH$_2$ | CH$_3$ | N-(4-iodo-3-methylphenyl)methanesulfonamide | | |

Preparation of Compounds

The above materials were generally prepared following Scheme 1 with the exception that N-methyl-2-piperidinemethyl chloride is used in place of acetoxylalkylhalides for the alkylation of the indole 1-position.

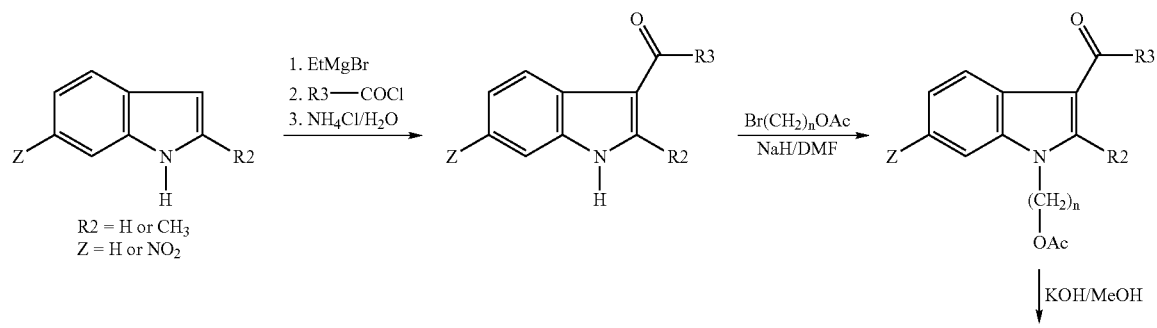

Scheme 1

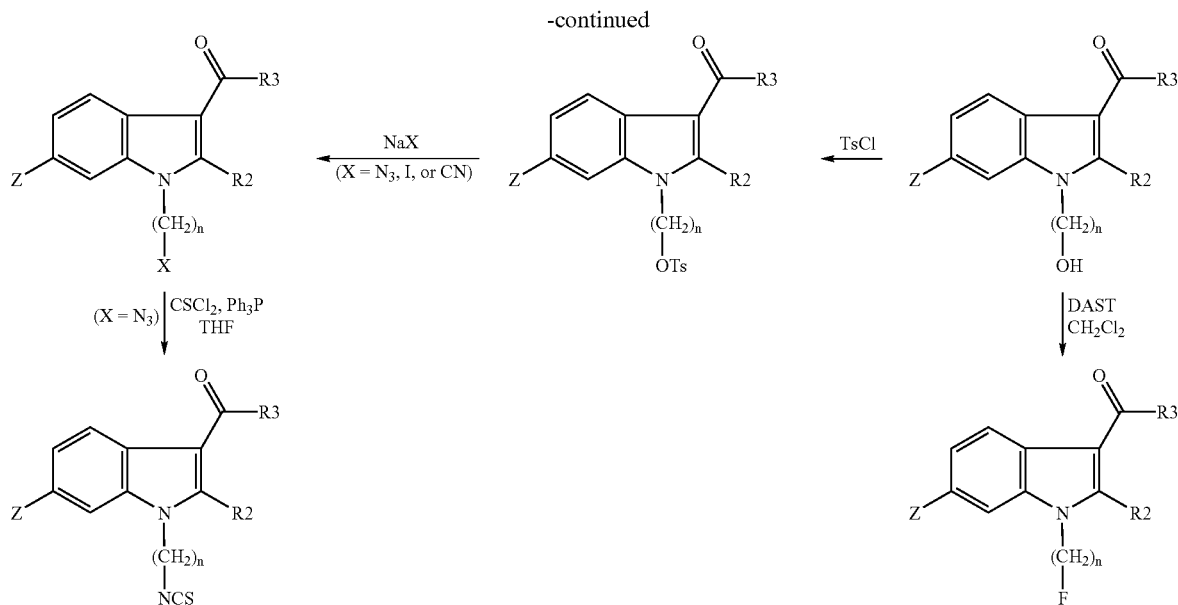

When Z=NO₂, the structures can be transformed to different substituents using methods outlined in Scheme 2.

Scheme 2

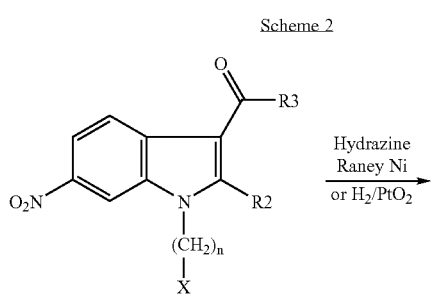

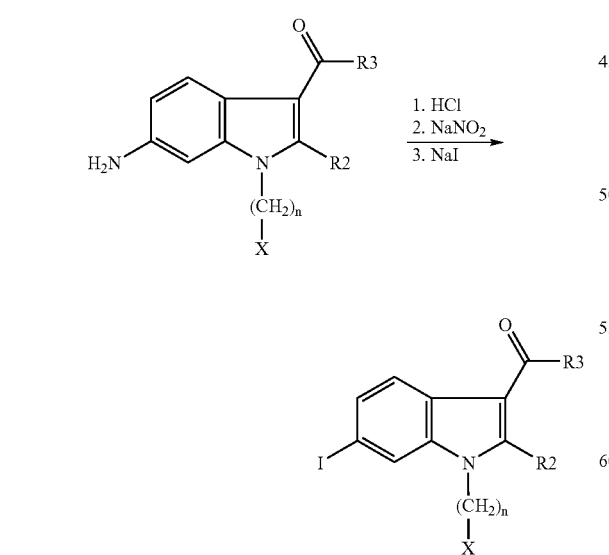

Scheme 3

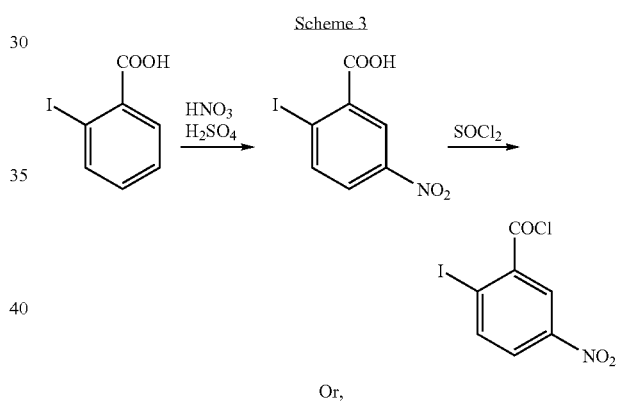

Or,

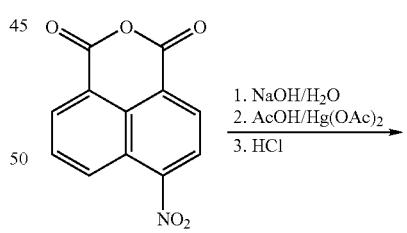

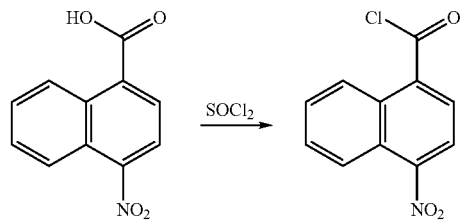

The commercially unavailable R3-COCl used in Scheme 1 can be prepared according to Scheme 3.

After these acid chlorides are connected at the indole 3-position, the nitro group therein can be further transformed into amino, iodo, azido, and isothiocyanate groups according to the methods outlined in Scheme 4.

Scheme 4

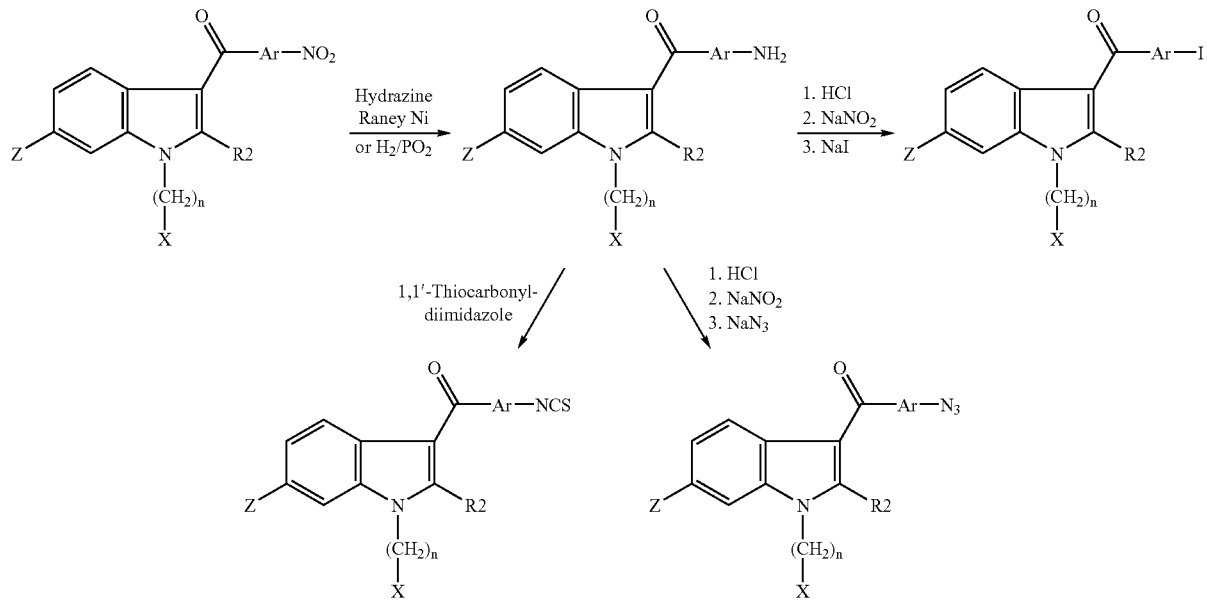

Examples of specific analogs were perpared as follows:

1-(N-Methyl-2-piperidinyl)methyl-3-(3-quinolinecarbonyl)-1H-indole

To the suspension of 200 mg (1.5 mmol) of anhydrous $AlCl_3$ in 8 ml absolute methylene chloride was added 287.4 mg (1.5 mmol) 3-quinolinecarbonyl chloride in 5 ml methylene chloride and the reaction mixture was stirred 30 min at room 22–25° C. The (N-Methyl-2-piperidinyl)methyl-1H-indole 228.3 mg (1.0 mmol) in 5 ml of methylene chloride was added by dropwise during 1.5 h and the mixture stirred 36 h. The reaction was work-up by addition of 20 ml 2M solution of sodium hydroxide and extracted by ethyl acetate (3×20 ml). The combined extract dried by sodium sulfate. After removing of solvents the rest (0.365 g) was purified by chromatography (silica gel, toluene-triethylamine, 10:1).

1-(N-Methyl-2-piperidinyl)methyl-3-(1-adamantanecarbonyl)-1H-indole

To the stirring solution of the diethyl aluminum chloride (1.5 ml 1 M soln. in hexane, 180.8 mg, 1.5 mmol) in 10 ml absolute methylene chloride was added at room temp. 298.0 mg (1.5 mmol) 1-adamantanecarbonyl chloride in 5 ml of methylene chloride and the reaction mixture was stirred 15 min. The solution of (N-Methyl-2-piperidinyl)methyl-1H-indole (228.3 mg, 1.0 mmol) in 5 ml of methylene chloride was added during 3 min and mixture was stirred and reflux 48 h. The reaction was work-up by addition of 20 ml 2M solution of sodium hydroxide and extracted by ethyl acetate (3×20 ml), washed to times by water and two times by brine. The combined extract dried by the mixture of sodium sulfate and potassium carbonate. After removing of solvents the rest was purified by chromatography (silica gel, methanol ethyl acetate 1:1).

1-(N-Methyl-2-piperidinyl)methyl-3-(2-iodo-5-cyano)benzoyl-1H-indole 1-(N-Methyl-2-piperidinyl)methyl-3-(2-iodo-5-amino) benzoyl-1H-indole (111.6 mg, 0.236 mmol) was dissolved in 3 ml of water containing 43 mg (1.179 mmol) of hydrogen chloride (101 mkl 38% HCl in 3 ml $H_2O$). The this solution was added at stirring sodium nitrite 16.64 mg (0.241 mmol) in 1 ml of water at 0° C. After 1 h the obtained diazonium salt was gradually added to solution of cuprous cyanide (23.5 mg, 0.264 mmol) in sodium cyanide (28.25 mg (0.528 mmol) in 1 ml of water at 60° C. The reaction mixture was diluted by water, extracted ethyl acetate (3×15 ml), dried sodium sulfate and after removing of solvent purified by chromatography (silica gel, methanol-ethyl acetate, 1:2).

A person of ordinary skill in the art, understanding the disclosures for the general preparation and specific preparation examples would know how to modify the disclosed procedures to achieve the above listed analogs.

The prepared cannabinoid compounds were tested for CB2 receptor binding affinity and for CB1 receptor affinity (to determine selectivity for the CB2 receptor). As used herein, "binding affinity" is represented by the $IC_{50}$ value which is the concentration of an analog required to occupy the 50% of the total number (Bmax) of the receptors. The lower the $IC_{50}$ value, the higher the binding affinity. As used herein a compound is said to have "binding selectivity" if it has higher binding affinity for one receptor compared to the other receptor; e.g. a compound that has an $IC_{50}$ of 0.1 nM for CB1 and 10 nM for CB2, is 100 times more selective for the CB1 receptor. The binding affinities ($K_i$) are expressed in nanomoles (nM).

For the CB1 receptor-binding studies, membranes were prepared from rat forebrain membranes according to the procedure of P. R. Dodd et al; *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al; *Determination and Characterization of a Cannabinoid Receptor in a Rat Brain*, Mol. Pharmacol., 34, 605–613 (1988) and A. Charalambous et al; "5'-azido $^8$-THC: A Novel Photoaffinity Label for the Cannabinoid Receptor", *J. Med. Chem.*, 35, 3076–3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4.The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials at 30° C. for 1 hour. The samples were immediately filtered using a Packard Filtermate 196 and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Non-specific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940.The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al; "Relationship Between the Inhibition Constant ($K_i$) and the concentration of Inhibitor which causes 50% Inhibition ($IC_{50}$) of an Enzymatic Reaction", *Biochem. Pharmacol.*, 22, 3099–3102, (1 973), which is incorporated by reference herein.

For the CB2 receptor binding studies, membranes were prepared from frozen mouse spleen essentially according to the procedure of P. R. Dodd et al; "A Rapid Method for Preparing Synaptosomes: Comparison with Alternative Procedures", *Brain Res.*, 226, 107–118 (1981) which is incorporated by reference herein. Silanized centrifuge tubes were used throughout to minimize receptor loss due to adsorption. The CB2 binding assay was conducted in the same manner as the CB1 binding assay. The binding affinities ($K_i$) were also expressed in nanomoles (nM). The structures, binding affinities and selectivities are summarized in Table 1.

As can be seen from the results in TABLES 1 and 2, some of the compounds, for example, 2-7, show a high selectivity for the CB2 receptor. The inventive compounds described herein have high potential when administered in therapeutically effective amounts for providing a physiological effect useful to treat a variety of disease conditions. Naturally, the invention also encompasses any physiologically acceptable salts, diasteromers, enantiomers, double bond isomers and mixtures of the above inventive compounds.

In addition, some of the iodide and fluoride containing compounds, for example, 2-7 or 2-24, are potential radioactive probes which would be useful for imaging in vivo the distribution of cannabinoid receptors. Further, azido containing compounds would be useful as affinity probes for characterizing binding pockets of cannabinoid receptors.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. A compound of the formula below, or the physiologically acceptable salts, diasteromers, enantiomers, double bond isomers, or mixtures thereof:

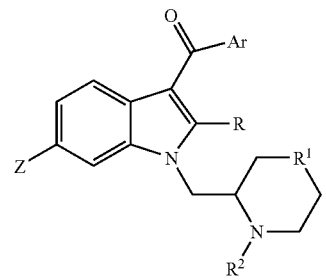

wherein:
Z is hydrogen;
R is hydrogen;
$R^1$ is selected from NH, O, S or $CH_2$;
$R^2$ is selected from $CH_3$, $CF_3$, $CH_2C\equiv CH$, $CH_2CH_2=CH_2$ or $CH_2Ph$; and
Ar is selected from; phenyl with no more than two substituents each independently selected from amino, halogen, hydroxy, nitro, nitroso, azido, isothiocyanato, cyano; COOH, $CONR^3R^4$ where $R^3$ and $R^4$ are each independently selected from H, alkyl or substituted alkyl, $NCOR^3R^4$ where $R^{b\ 3}$ and $R^4$ are each independently selected from H, alkyl, substituted alkyl or $CF_3$ and $NSO_2R^3R^4$ where $R^3$ and $R^4$ are each independently selected from H, alkyl, substituted alkyl or $CF_3$; naphthyl with no more than two substituents each independently selected from amino, halogen, hydroxy, nitro, nitroso, azido, isothiocyanato, cyano or COOH, $CONR^3R^4$ where $R^3$ and $R^4$ are each independently selected from H, alkyl or substituted alkyl, $NCOR^3R^4$ where $R^3$ and $R^4$ are each independently selected from H, alkyl, substituted alkyl or $CF_3$, $NSO_2R^3R^4$ where $R^3$ and $R^4$ are each independently selected from H, alkyl, substituted alkyl or $CF_3$; or a salt of any of the above, with the provisos that:
if $R^2$ is $CH_3$ or $CH_2Ph$; then Ar cannot be unsubstituted phenyl; phenyl substituted by from one to two substituents selected from the group consisting of fluorine, chlorine, bromine, hydroxy, nitro and amino; 1- or 2-naphthyl or 1- or 2-naphthyl substituted by from one to two substituents selected from the group consisting of fluorine, chlorine and bromine; and
if $R^1$ is $CH_2$ and $R^2$ is $CH_3$; then Ar cannot be phenyl substituted by from one to two halogen atoms; 1- or 2-naphthyl or 1- or 2-naphthyl substituted by from one to two substituents selected from the group consisting of halogen, hydroxy, and cyano; anthracenyl or anthracenvl substituted by from one to two substituents selected from the group consisting of fluorine, chlorine, bromine hydroxy, and cyano.

2. The compound of claim 1, wherein:
Z is H;
R is H;

R[1] is CH$_2$;
R[2] is CH$_3$; and
Ar is 2-iodo-5-nitrophenyl.

3. A pharmaceutical preparation comprising a therapeutically effective amount of a compound of the formula below, or the physiologically acceptable salts, diasteromers, enantiomers, double bond isomers or mixtures thereof:

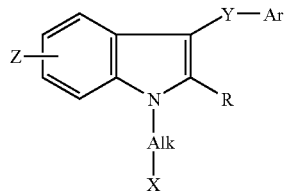

wherein:
Z is hydrogen;
Alk is selected from an alkyl group or a substituted alkyl group;
X is selected from 6 member heterocyclic ring, including at least one heteroatom independently selected from oxygen, nitrogen and sulfur; a substituted 6 member heterocyclic ring, including at least one heteroatom independently selected from oxygen, nitrogen and sulfur; and the Alk moiety bonds to a ring carbon atom of the X moiety;
R is selected from hydrogen, an alkyl group or a substituted alkyl group;
Y is carbonyl ; and
Ar is selected from phenyl; naphthyl; 9-anthracenyl; an aliphatic bicyclic ring; any of the above with no more than two substituents each independently selected from amino, halogen, hydroxy, nitro, nitroso, azido, isothiocyanato, cyano, COOH, CONR$^3$R$^4$ where R$^3$ and R$^4$ are each independently selected from H, alkyl or substituted alkyl, NCOR$^3$R$^4$ where R$^3$ and R$^4$ are each independently selected from H, alkyl, substituted alkyl or CF$_3$, NSO$_2$R$^3$R$^4$ where R$^3$ and R$^4$ are each independently selected from H, alkyl, substituted alkyl or CF$_3$; or a salt of any of the above;
with the provisos that:
if X is an unsubstituted 6 member heterocyclic ring or a 6 member heterocyclic ring substituted with at least one member selected from the group consisting of alkyl, hydroxy, benzyl or lower alkoxvbenzyl; and R is H or an alkyl group; then Ar cannot be unsubstituted phenyl; phenyl substituted by from one to two substituents selected from the group consisting of fluorine, chlorine, bromine, hydroxy, nitro and amino; 1- or 2-naphthyl or 1- or 2-naphthyl substituted by from one to two substituents selected from the group consisting of fluorine, chlorine and bromine;
if X is an unsubstituted 6 member heterocyclic ring or an alkyl substituted 6 member heterocyclic ring; and R is H or an alkyl group; then Ar cannot be phenyl substituted by from one to two halogen atoms; 1- or 2-naphthyl or 1- or 2-naphthyl substituted by from one to two substituents selected from the group consisting of halogen, hydroxy and cyano; anthracenyl or anthracenyl substituted by from one to two substituents selected from the group consisting of halogen, hydroxy, and cyano; and
if X is an unsubstituted 6 member heterocyclic ring including both nitrogen and oxygen as ring heteroatoms: and R is H or an alkyl group: then Ar cannot be phenyl substituted by cyano; naphthyl substituted by a single substituent selected from the group consisting of hydroxy, nitro, amino, and isothiocyano: or anthracenyl.

4. The pharmaceutical preparation of claim 3 wherein:
Z is H;
Alk is CH$_2$;
X is a 6 member heterocyclic ring containing a single hetero nitrogen atom;
R is H;
Y is carbonyl; and
Ar is iodo, nitrophenyl.

5. The pharmaceutical preparation of claim 3 wherein the compound is

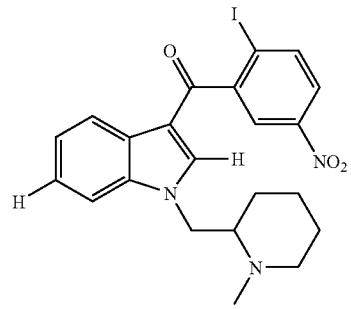

including physiologically acceptable salts, diasteromers, enantiomers, double bond isomers, or mixtures thereof.

6. The compound of claim 1 of the formula:

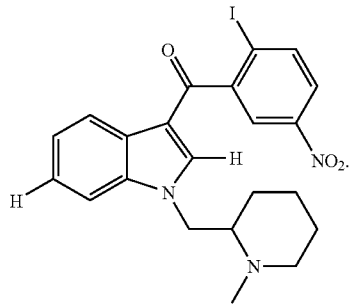

7. A compound of the formula, or the physiologically acceptable salts, diasteromers, enantiomers, double bond isomers, or mixtures thereof:

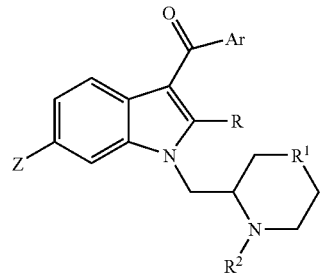

wherein:
Z is hydrogen;
R is hydrogen;

$R^1$ is selected from NH, O, S or $CH_2$;

$R^2$ is selected from $CH_3$, $CF_3$, $CH_2C\equiv CH$, $CH_2CH=CH_2$ or $CH_2Ph$; and Ar is selected from an aliphatic bicyclic ring or an aliphatic bicyclic ring with no more than two substituents each independently selected from amino, halogen, hydroxy, nitro, nitroso, azido, isothiocyanato, cyano, COOH, $CONR^3R^4$ where $R^3$ and $R^4$ are each independently selected from H, alkyl or substituted alkyl, $NCOR^3R^4$ where $R^3$ and $R^4$ are each independently selected from H, alkyl, substituted alkyl, or $CF_3$, and $NSO^2R^3R^4$ where $R^3$ and $R^4$ are each independently selected from H, alkyl, substituted alkyl or $CF_3$; or a salt of any of the above, with the proviso that:

if R is H or alkyl; and $R^1$ is $CH_2$; and $R^2$ is $CH_3$; then Ar cannot be 1,2,3,4-tetrahydronaphthyl or 1,2,3,4-tetrahydronaphthyl substituted by from one to two substituents selected from the group consisting of halogen, hydroxy and cyano.

8. The compound of claim 1, wherein:

Z is H;

R is H;

$R^1$ is $CH_2$;

$R^2$ is $CH_3$; and

Ar is phenyl substituted with a single I atom and a single CN moiety.

9. The compound of claim 1, wherein:

Z is H;

R is H;

$R^1$ is $CH_2$;

$R^2$ is $CH_3$; and

Ar is

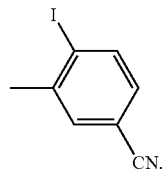

10. The pharmaceutical preparation of claim 3, wherein:

Alk is $CH_2$;

X is a substituted 6 member heterocyclic ring including a single nitrogen atom;

R is H; and

Ar is phenyl substituted with a single I atom and a single CN moiety.

11. The pharmaceutical preparation of claim 3, wherein:

Alk is $CH_2$;

X is a substituted 6 member heterocyclic ring including a single nitrogen atom;

R is H; and

Ar is

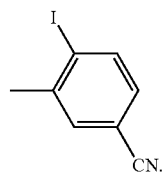

* * * * *

UNITED STATES PATENT AND TRADEMARK OFFICE
CERTIFICATE OF CORRECTION

PATENT NO. : 7,173,027 B2  Page 1 of 1
APPLICATION NO. : 10/470359
DATED : February 6, 2007
INVENTOR(S) : Makriyannis et al.

It is certified that error appears in the above-identified patent and that said Letters Patent is hereby corrected as shown below:

Column 20:

Line 30, delete "$CH_2CH_2 = CH_2$" and substitute --$CH_2CH = CH_2$--.

Line 34, after "cyano" delete ";" and substitute --,--.

Line 37, after "$CF_3$" insert --,--.

Lines 61-62, delete "anthra-cenvl" and substitute --anthra-cenyl--.

Column 21:

Line 48, delete "alkoxvbenzyl" and substitute --alkoxybenzyl--.

Column 22:

Line 1, after "oms" delete ":" and substitute --;--.

Line 1, after "group" delete ":" and substitute --;--.

Line 4, after "isothiocyano" delete ":" and substitute --;--.

Column 23:

Line 12, delete "$NSO^2R^3R^4$" and substitute --$NSO_2R^3R^4$--.

Signed and Sealed this

Thirteenth Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,173,027 B2  Page 1 of 1
APPLICATION NO. : 10/470359
DATED : February 6, 2007
INVENTOR(S) : Makriyannis et al.

It is certified that error appears in the above-identified patent and that said Letters Patent is hereby corrected as shown below:

Column 20:

Line 30, delete "$CH_2CH_2 = CH_2$" and substitute --$CH_2CH = CH_2$--.

Line 34, after "cyano" delete ";" and substitute --,--.

Line 37, after "$CF_3$" insert --,--.

Lines 61-62, delete "anthra-cenvl" and substitute --anthra-cenyl--.

Column 21:

Line 48, delete "alkoxvbenzyl" and substitute --alkoxybenzyl--.

Column 22:

Line 1, after "oms" delete ":" and substitute --;--.

Line 1, after "group" delete ":" and substitute --;--.

Line 4, after "isothiocyano" delete ":" and substitute --;--.

Column 23:

Line 12, delete "$NSO^2R^3R^4$" and substitute --$NSO_2R^3R^4$--.

Signed and Sealed this

Twenty-seventh Day of November, 2007

JON W. DUDAS
*Director of the United States Patent and Trademark Office*